›

US005800825A

United States Patent [19]
McMullen

[11] Patent Number: 5,800,825
[45] Date of Patent: Sep. 1, 1998

[54] MASCARA HAVING ENHANCED DRYING CAPABILITY

[76] Inventor: Alexandra McMullen, 673 Washington Blvd., Marina Del Rey, Calif. 90292

[21] Appl. No.: 745,605

[22] Filed: Nov. 8, 1996

[51] Int. Cl.⁶ ........................................ A61K 7/00
[52] U.S. Cl. ........................... 424/401; 424/70.7
[58] Field of Search ..................... 424/401, 70.7, 424/63

[56] References Cited

U.S. PATENT DOCUMENTS

| | | |
|---|---|---|
| D. 320,671 | 10/1991 | Hoenig . |
| 4,632,136 | 12/1986 | Kingsford . |
| 4,988,502 | 1/1991 | Ounanian et al. . |
| 5,053,220 | 10/1991 | Arraudeau et al. . |
| 5,053,221 | 10/1991 | Robertson et al. . |
| 5,451,610 | 9/1995 | Krzysik . |
| 5,460,808 | 10/1995 | Mausner . |
| 5,480,632 | 1/1996 | Orr et al. .................. 424/63 |
| 5,534,247 | 7/1996 | Franjac et al. ............ 424/70.7 |
| 5,614,200 | 3/1997 | Bartholomey et al. ...... 424/401 |

*Primary Examiner*—Thurman K. Page
*Assistant Examiner*—Sharon Howard
*Attorney, Agent, or Firm*—Workman, Nydegger & Seeley

[57] ABSTRACT

Dry formula mascaras which have enhanced drying characteristics are made using a specially formulated drying system which includes solvents and hardening agents. The drying system comprises a mixture of ammonium acrylate copolymer, propylene glycol, potassium octoxynol-12 phosphate, and nonoxynol-10. The inventive mascaras may also include water as a diluent and solvent, waxes that act as a binder, surfactant, emulsifying agent, and conditioning agent, PVP, which acts as a binder and emulsifier stabilizer, and other components such as humectants, conditioning agents, emulsifier stabilizers, thickeners, emollients, antimicrobial agents and suspending agents.

16 Claims, No Drawings

MASCARA HAVING ENHANCED DRYING CAPABILITY

BACKGROUND OF THE INVENTION

1. The Field of the Invention

The present invention is in the field of cosmetics, particularly in the field of mascaras that are applied to eyelashes. More particularly, the present invention relates to mascaras which are specially formulated to dry more quickly upon application compared to conventional mascaras.

2. The Relevant Technology

We live in an era when beauty and personal appearance are highly regarded. Both men and women are known to spend significant amounts of money in order to achieve physical beauty, or at least improve their appearance to some degree.

In particular, some women are known to show considerable attention to their facial features, including their eyelashes, Aside from fads in the past wherein women actually attached prosthetic (or false) eyelashes in order to enhance their length and perceived attractiveness, the beauty of eyelashes is enhanced today mainly by curling and/or applying mascara to the eyelashes. Curling of the eyelashes is typically carried out using an eyelash curling device equipped with tongs which are brought together manually in order pinch the eyelashes between an upper tong and a lower tong. Typically, the lower tong is equipped with a flexible compression strip in order to distribute the pressure more evenly and in a directed manner in order to effect proper curling of the eyelashes without significant breakage.

More recently, fashion magazines and other mouthpieces of the beauty industry have advocated heating the eyelash curling device by means of a blow dryer in order to cause the eyelashes to be curled more easily and more permanently. The concept of heating hair is known; however, the ability to reliably heat the eyelashes is problematic due to their relatively small size and close proximity to the eyes. Heating an eyelash curling device with a blow dryer has been an adequate, though not perfect, solution to the on-going dilemma of attaining well-curled eyelashes.

More recently, heating units separate and apart from the eyelash curling device have been developed, which are specially designed to reliably heat the eyelash curling device in a manner which makes eyelash curling both easier and safer. Remote heating apparatus designed to complement the unique mechanical features and functionality of eyelash curling devices are set forth in copending U.S. application Ser. No. 08/516,934 entitled "APPARATUS FOR REMOTELY HEATING AN EYELASH CURLING DEVICE" and filed Aug. 18, 1995, in the name of Alexandra McMullen, now issued as U.S. Pat. No. 5,590,669. For purposes of disclosing eyelash curling devices and means for remotely heating such devices, the foregoing application is incorporated herein by specific reference.

The other important and widely used eyelash beautification technique (mainly used by women) is the application of specially formulated eyelash cosmetics commonly known as "mascaras". Typically, mascaras are packaged in a narrow bottle into which an applicator brush is first inserted to pick up some of the mascara from the bottle and then withdrawn in order to apply the mascara by brushing it onto the undersides of the eyelashes. Conventional mascaras are generally wet when first applied and dry slowly over time. During the time when the mascara is still wet it is prone to smearing and transference onto the eyelids and other skin surrounding the eyes. Such smearing is usually considered to be unattractive and aesthetically unappealing and can detract from a woman's appearance much more than simply not applying the mascara in the first place. Moreover, certain public figures have been lampooned over their supposed and unseemly over use or misuse of mascara.

Because mascaras are essentially a paint or pigmented overlay that coats the surface of the eyelashes, mascaras can be used to alter the orientation and spacing of eyelashes. Because mascaras are typically applied using a curved application brush, mascaras can be used to create a degree of curling of the eyelashes. Once dry, the mascara can act as an adhesive-like material that maintains a certain degree of curl in the eyelashes. In addition, mascara causes eyelashes to appear thicker and more prominent.

However, mascara can, both intentionally and unintentionally, cause eyelashes to bunch or clump together such that the eyelashes appear to protrude from the eyelids as eyelash groups or clumps rather than as individual eyelashes. While some consider eyelash clumping to be gaudy, others undoubtedly consider it to be a fashion statement to be emulated (due to its common occurrence). Regardless of one's taste or proclivities regarding eyelash clumping, such clumping occurs mainly through the use of larger quantities of mascara than what is typically applied in order to attain more well-spread-apart and individually differentiated eyelashes. Naturally, if the mascara is wet and slow-drying to begin with when used in moderate amounts, increasing the amount of applied mascara only serves to exacerbate the difficulties associated with slow-drying mascara and greatly increases the drying time.

Because people typically apply cosmetics and perform other beautification techniques and toiletries during the same approximate time frame, the application of mascara and the curling of eyelashes using an eyelash curling device will normally occur in approximately the same time frame. However, conventional wet, slow-drying mascaras can cause problems if applied in conjunction with eyelash curling. If a woman first curls her eyelashes and then applies wet mascara, the wetness of the mascara could undue the curling effect previously attained by means of the eyelash curling device. This can be understood by noting that curled hair relaxes or looses its curl upon getting wet or when exposed to even slight moisture.

On the other hand, applying the mascara before curling the eyelashes could create a different kind of problem due to the slowness in drying of the mascara. If a mascara takes, for example, ten minutes to fully dry, a woman must wait ten minutes before curling her eyelashes after applying the mascara. While some people might have the luxury of time, others, such as those in the beauty profession or those who are simply on the way to work or otherwise on the run, do not have luxurious amounts of time.

In light of the foregoing, it would be an advancement in the cosmetic art to provide improved mascara compositions that were initially drier than typical mascaras presently used.

In addition, it would be an improvement in the cosmetic art to provide mascara compositions that were able to dry more quickly than mascaras presently used.

It would be an additional advancement in the cosmetic art to provide mascaras which were more compatible with the use of eyelash curling devices, whether heated or not heated.

Moreover, it would be an advancement in the cosmetic art to provide dry formula mascaras which facilitated their use either before or after the eyelash curling process and which enhanced rather than detracted from the curling process.

Such dry formula mascaras are disclosed and claimed herein.

SUMMARY AND OBJECTS OF THE INVENTION

The present invention relates to mascaras that are applied to eyelashes in order to enhance their attractiveness. Whereas conventional mascaras typically go on wet and remain wet over a significant period of time, the mascaras of the present invention are specially formulated in order to increase their drying ability. In this manner, the mascaras of the present invention overcome the problems associated with wet, slow drying mascaras.

The mascaras of the present invention dry more quickly and therefore are less prone to be smeared onto the user's eyelids or other skin surrounding the eyes. In addition, a fast drying mascara is more compatible with the use of eyelash curling devices, whether used before or after the curling process. If used before, the fast drying mascara allows the eyelashes to be curled in a much quicker time frame after application of the mascara. If applied after curling, the fast drying mascaras of the present invention will reduce the tendency to cause drooping or uncurling of the eyelashes.

The main component within the mascaras of the present invention that allows for quicker drying is the specially formulated drying system. Although many fast-drying volatile solvents might work to create faster drying mascara, the drying system that appears to provide adequately fast drying while maintaining the ability to remove the mascara with water is a mixture of the following components: ammonium acrylate copolymer, propylene glycol, potassium octoxynol-12 phosphate, and nonoxynol-10. The foregoing mixture includes solvents and setting agents. Volatile solvents and other setting agents might be used in conjunction with, or in place of, the foregoing components of the drying system, although volatile solvents tend to yield mascara that is more waterproof. While this makes it more difficult to remove, it might have the desired beneficial effect of making the mascara less prone to running or streaking if were to get wet by, e.g., crying, swimming, or raining. The ability to remove the mascara with water or other makeup removers is preferred because mascara that is difficult to remove can lead to damage or removal of the eyelashes.

In addition to the drying system, an antifoaming agent such as simethicone has been found to be useful in yielding stable, dry formula mascaras. In addition, the preferred mascara can also include one or more of the following: water (diluent), beeswax (binder, surfactant, emulsifying agent), carnauba (binder, hair conditioning agent), PVP (binder, emulsion stabilizer), additional propylene glycol (humectant, skin conditioning agent), glyceryl stearate SE (emulsifier, stabilizer), stearic acid (thickener, emulsifier), propylene glycol stearate SE (emulsifier), oleic acid (emulsifier, intermediate), polybutene (emollient, lubricant, moisturizer), magnesium aluminum silicate (thickener), phenoxyethanol (antimicrobial), cellulose gum (thickener, suspending agent), methylparaben (preservative), propylparaben (preservative), tetrasodium EDTA (chelating agent), pigments, and iron oxide (colorant). The foregoing ingredients are given by way of example, not by limitation. Any equivalent component could be substituted for any of the above ingredients in order to impart to the mascara desired properties and characteristics.

In view of the foregoing, it is an object of the present invention to provide improved mascara compositions that are initially dryer than typical mascaras presently used.

In addition, it is an object of the present invention to provide mascara compositions that are able to dry more quickly than mascaras presently used.

It is an additional object and feature of the present invention to provide mascaras which are more compatible with the use of eyelash curling devices, whether heated or not heated.

It is yet a further object of the present invention to provide dry formula mascaras which facilitate their use either before or after the eyelash curling process which enhance rather than detract from the curling process.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The present invention relates to specially formulated mascaras that are dryer when initially applied to the eyelashes and which dry more quickly than conventional mascaras presently used. Conventional mascaras typically have a wetter formulation such that they go on wet and remain wet over a significant period of time. Thus, the mascaras of the present invention overcome many problems that are associated with more wet, more slow drying mascaras.

The inventive mascaras are specially formulated to dry more quickly. They therefore reduce the likelihood that they will be smeared onto the eyelids or other skin surrounding the eyes. In addition, the fast drying mascaras of the present invention facilitate their use with eyelash curling devices. Moreover, the fast drying mascaras yield better results whether used before or after the curling process. If used before, the fast drying mascara allows the eyelashes to be curled much sooner after application of the mascara since the drying time is greatly reduced. If applied after curling, the fast drying mascaras of the present invention will reduce the tendency of wetter mascaras to cause drooping or uncurling of the eyelashes. (Note that exposure of curled hair in general to even slight amounts of moisture is known to relax the curl, particularly if the curl is only temporary, such as curls introduced by the application of heat).

In order to more broadly teach the different embodiments that may comprise the present invention, the various components of the present invention will not only be identified but described in terms of the function that they impart. Hence, one of ordinary skill in the art will know that through routine experimentation, one or more of the ingredients could be substituted or replaced with one or more equivalent ingredients that impart the desired properties. The only limitation is that the mascara formulation be fast drying.

By "fast drying" Applicant means that the mascaras of the present invention are preferably able to dry sufficiently so that they will not easily smear or be wet to the touch in less than about 3 minutes after application of the mascara to the eyelashes. More preferably, the mascaras will be sufficiently dry in less about 2 minutes after application, and most preferably in less than about 1 minute after application of the mascara.

While the preferred mascara will be sufficiently water soluble even after drying such that it can be removed by washing off with water, it may be preferable for some applications to alter the identities and/or concentrations of the components in order to obtain a mascara that is more resistant to water. In this fashion, it will be possible to formulate a mascara that will be more permanent and resistant to the deleterious effects of moisture encountered throughout the day (e.g., pool water, rain, tears).

The component within the mascaras of the present invention that is responsible for quicker drying is the drying system. The drying system that appears to provide adequately fast drying while maintaining the ability to remove the mascara with water or other eye makeup removers when desired comprises a mixture of the following components: ammonium acrylate copolymer, propylene glycol, potassium octoxynol-12 phosphate, and nonoxynol-10. The foregoing mixture includes solvents and setting agents. The mixture comprising the drying system may be included in an amount in a range from about 1% to about 50% by weight of the mascara. Preferably, the drying system is included in an amount in a range from about 4% to about 40% by weight of the mascara composition, more preferably in a range from about 5% to about 30% by weight, and most preferably in a range from about 8% to about 20% by weight of the composition.

In order for the mascara to have the proper consistency and in order to obtain good dispersion of the various pigments and other components, the mascara generally includes a diluent. The diluent can include one or more of a variety of generally polar and less volatile solvents. A preferred diluent is water. Others may include alcohols, aldehydes, ketones, esters, and the like. The diluent is preferably included in an amount in a range from about 5% to about 90% by weight of the mascara composition, more preferably in a range from about 20% to about 70% by weight, and most preferably in a range from about 30% to about 50% by weight of the composition.

An antifoaming agent, such as simethicone, has been found to be useful in yielding stable, dry formula mascaras. The antifoaming agent is preferably included in an amount in a range from about 0.01% to about 5% by weight of the mascara composition, more preferably in a range from about 0.05% to about 3% by weight, and most preferably in a range from about 0.1% to about 1% by weight of the composition.

As with all mascaras, pigments known in the art can be employed in whatever range is desired to yield a mascara having the desired color and intensity of color. Iron oxide can be used alone or in conjunction with other pigments known in the art and may be included in an amount up to about 20% by weight of the mascara, more preferably in a range from about 2% to about 15% by weight and most preferably in a range from about 5% to about 10% by weight of the mascara. In addition, one or more of the following ingredients may be included or be substituted with an appropriate equivalent. They are given by way of example, not by limitation. The three ranges that are given are in order of preferredness, with the first range being preferred, the second range being more preferred, and the third range being most preferred.

Beeswax (binder, surfactant, emulsifying agent):
about 0–30 wt. %; about 3–20 wt. %; about 5–15 wt. %;
Carnauba (binder, hair conditioning agent):
about 0–30 wt. %; about 3–20 wt. %; about 5–15 wt. %;
PVP (binder, emulsion stabilizer):
about 0–25 wt. %; about 3–15 wt. %; about 5–12 wt. %;
Propylene Glycol (humectant, skin conditioning agent):
about 0–20 wt. %; about 2–15 wt. %; about 3–10 wt. %;
Glyceryl Stearate SE (emulsifier, stabilizer):
about 0–15 wt. %; about 1–10 wt. %; about 2–8 wt. %;
Stearic Acid (thickener, emulsifier):
about 0–10 wt. %; about 0.5–8 wt. %; about 1–5 wt. %;
Propylene Glycol Stearate SE (emulsifier):
about 0–10 wt. %; about 0.3–6 wt. %; about 0.7–3 wt. %;
Oleic Acid (emulsifier, intermediate):
about 0–10 wt. %; about 0.3–6 wt. %; about 0.7–3 wt. %;
Polybutene (emollient, lubricant, moisturizer):
about 0–10 wt. %; about 0.3–6 wt. %; about 0.7–3 wt. %;
Magnesium Aluminum Silicate (thickener):
about 0–5 wt. %; about 0.01–3 wt. %; about 0.1–1 wt. %;
Phenoxyethanol (antimicrobial):
about 0–5 wt. %; about 0.01–3 wt. %; about 0.1–1 wt. %;
Cellulose Gum (thickener, suspending agent):
about 0–5 wt. %; about 0.01–3 wt. %; about 0.1–1 wt. %;
Methylparaben (preservative):
about 0–5 wt. %; about 0.01–3 wt. %; about 0.1–1 wt. %;
Propylparaben (preservative):
about 0–5 wt. %; about 0.01–3 wt. %; about 0.1–1 wt. %;
Tetrasodium EDTA (chelating agent):
about 0–5 wt. %; about 0.01–3 wt. %; about 0.1–1 wt. %;

EXAMPLES OF THE PREFERRED EMBODIMENTS

In order to more fully teach what the Applicant regards as her invention, the following examples are given. It should be understood that the formulations set forth in the Examples are given by way of example only and are not to be construed as limiting the scope of the invention, except so far as they yield dry formula mascaras having the desired properties and characteristics.

Example 1

A dry formula mascara was manufactured that had the following components, with the percentages being given by weight of the mascara:

| | |
|---|---|
| Water | 40% |
| Beeswax | 9% |
| Drying System (ammonium acrylate copolymer, propylene glycol, potassium octoxynol-12 phosphate, and nonoxynol-10) | 9% |
| Carnauba | 9% |
| PVP | 7% |
| Propylene Glycol | 6% |
| Glyceryl Stearate SE | 5% |
| Stearic Acid | 2.5% |
| Propylene Glycol Stearate SE | 2% |
| Oleic Acid | 2% |
| Polybutene | 1.5% |
| Magnesium Aluminum Silicate | 1% |
| Phenoxyethanol | 1% |
| Cellulose Gum | 1% |
| Methylparaben | 1% |
| Propylparaben | 1% |
| Tetrasodium EDTA | 1% |
| Simethicone | 1% |

The mascara also included pigments known in the art but not listed here. The foregoing mascara composition was able to become sufficiently dry such that it would not easily smear and was relatively dry to the touch in about 60 seconds after first applying the mascara to the eyelashes. After drying, the mascara remained sufficiently water soluble such that it could be easily removed with water or other eye makeup removers when desired.

Example 2

A dry formula mascara was manufactured that had the following components, with the percentages being given by weight of the mascara:

| | |
|---|---|
| Water | 35% |
| Beeswax | 10% |
| Drying System (ammonium acrylate copolymer, propylene glycol, potassium octoxynol-12 phosphate, and nonoxynol-10) | 10% |
| Carnauba | 10% |
| PVP | 8% |
| Propylene Glycol | 7% |
| Glyceryl Stearate SE | 5% |
| Stearic Acid | 2.5% |
| Propylene Glycol Stearate SE | 2% |
| Oleic Acid | 2% |
| Polybutene | 1.5% |
| Magnesium Aluminum Silicate | 1% |
| Phenoxyethanol | 1% |
| Cellulose Gum | 1% |
| Methylparaben | 1% |
| Propylparaben | 1% |
| Tetrasodium EDTA | 1% |
| Simethicone | 1% |

The mascara also included pigments known in the art but not listed here. The foregoing mascara composition was able to become sufficiently dry such that it would not easily smear and was relatively dry to the touch in about 60 seconds after first applying the mascara to the eyelashes. After drying, the mascara remained sufficiently water soluble such that it could be easily removed with water or other eye makeup removers when desired.

Example 3

A dry formula mascara was manufactured that had the following components, with the percentages being given by weight of the mascara:

| | |
|---|---|
| Water | 45% |
| Beeswax | |
| Drying System (ammonium acrylate copolymer, propylene glycol, potassium octoxynol-12 phosphate, and nonoxynol-10) | 8% |
| Carnauba | 8% |
| PVP | 6% |
| Propylene Glycol | 5% |
| Glyceryl Stearate SE | 5% |
| Stearic Acid | 2.5% |
| Propylene Glycol Stearate SE | 2% |
| Oleic Acid | 2% |
| Polybutene | 1.5% |
| Magnesium Aluminum Silicate | 1% |
| Phenoxyethanol | 1% |
| Cellulose Gum | 1% |
| Methylparaben | 1% |
| Propylparaben | 1% |
| Tetrasodium EDTA | 1% |
| Simethicone | 1% |

The mascara also included pigments known in the art but not listed here. The foregoing mascara composition was able to become sufficiently dry such that it would not easily smear and was relatively dry to the touch in about 60 seconds after first applying the mascara to the eyelashes. After drying, the mascara remained sufficiently water soluble such that it could be easily removed with water or other eye makeup removers when desired.

Example 4

A dry formula mascara was manufactured that had the following components, with the percentages being given by weight of the mascara:

| | |
|---|---|
| Water | 40% |
| Beeswax | 10% |
| Drying System (ammonium acrylate copolymer, propylene glycol, potassium octoxynol-12 phosphate, and nonoxynol-10) | 10% |
| Carnauba | 10% |
| PVP | 8% |
| Propylene Glycol | 7% |
| Glyceryl Stearate SE | 5% |
| Stearic Acid | 2% |
| Propylene Glycol Stearate SE | 1.5% |
| Oleic Acid | 1.5% |
| Polybutene | 1.5% |
| Magnesium Aluminum Silicate | 0.5% |
| Phenoxyethanol | 0.5% |
| Cellulose Gum | 0.5% |
| Methylparaben | 0.5% |
| Propylparaben | 0.5% |
| Tetrasodium EDTA | 0.5% |
| Simethicone | 0.5% |

The mascara also included pigments known in the art but not listed here. The foregoing mascara composition was able to become sufficiently dry such that it would not easily smear and was relatively dry to the touch in about 60 seconds after first applying the mascara to the eyelashes. After drying, the mascara remained sufficiently water soluble such that it could be easily removed with water or other eye makeup removers when desired.

In addition to the foregoing examples, which describe the manufacture of actual mascara compositions, Applicant now presents hypothetical examples in order to more fully teach the variety of compositions encompassed by the present invention. While hypothetical in nature, the following examples are based on actual test mixes that were carried or based on what one of ordinary skill in the art would expect to be within the scope of the present invention.

Example 5

A dry formula mascara is manufactured that has the following components, with the percentages being given by weight of the mascara:

| | |
|---|---|
| Water | 50% |
| Beeswax | 10% |
| Drying System (ammonium acrylate copolymer, propylene glycol, potassium octoxynol-12 phosphate, and nonoxynol-10) | 20% |
| Carnauba | 10% |
| PVP | 9% |
| Simethicone | 1% |

The mascara also includes pigments known in the art but not listed here. The foregoing mascara composition is able to become sufficiently dry such that it will not easily smear and is relatively dry to the touch in less than about 2 minutes after first applying the mascara to the eyelashes. After drying, the mascara remains sufficiently water soluble such that it can be easily removed with water or other eye makeup removers when desired.

Example 6

A dry formula mascara is manufactured that has the following components, with the percentages being given by weight of the mascara:

| | |
|---|---|
| Water | 70% |
| Drying System (ammonium acrylate copolymer, propylene glycol, potassium octoxynol-12 phosphate, and nonoxynol-10) | 20% |
| Carnauba | 9% |
| Simethicone | 1% |

The mascara also includes pigments known in the art but not listed here. The foregoing mascara composition is able to become sufficiently dry such that it will not easily smear and is relatively dry to the touch in less than about 3 minutes after first applying the mascara to the eyelashes. After drying, the mascara remains sufficiently water soluble such that it can be easily removed with water or other eye makeup removers when desired.

Example 7

A dry formula mascara is manufactured that has the following components, with the percentages being given by weight of the mascara:

| | |
|---|---|
| Water | 30% |
| Beeswax | 15% |
| Drying System (ammonium acrylate copolymer, propylene glycol, potassium octoxynol-12 phosphate, and nonoxynol-10) | 30% |
| Carnauba | 10% |
| PVP | 9% |
| Glyceryl Stearate SE | 4% |
| Simethicone | 2% |

The mascara also includes pigments known in the art but not listed here. The foregoing mascara composition is able to become sufficiently dry such that it will not easily smear and is relatively dry to the touch in less than about 30 seconds after first applying the mascara to the eyelashes. After drying, the mascara remains sufficiently water soluble such that it can be easily removed with water or other eye makeup removers when desired.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A mascara composition having enhanced drying capability comprising a diluent, an emulsifying agent, an antifoaming agent, a pigment, and a drying system included in an amount in a range from about 1% to about 50% by weight of the composition, the drying system consisting essentially of ammonium acrylate copolymer, propylene glycol, potassium octoxynol-12 phosphate, and nonoxynol-10.

2. A mascara composition having enhanced drying capability comprising a diluent, an emulsifying agent, an antifoaming agent, a moisturizer, a pigment, and a drying system included in an amount in a range from about 4% to about 40% by weight of the composition, the drying system consisting essentially of ammonium acrylate copolymer, propylene glycol, potassium octoxynol-12 phosphate, and nonoxynol- 10, said antifoaming agent including simethicone.

3. A mascara composition having enhanced drying capability comprising:

a. water in an amount of about 20–70 wt. %;
b. a drying system in an amount of about 4–40 wt. % and consisting essentially of ammonium acrylate copolymer, propylene glycol, potassium octoxynol-12 phosphate, and nonoxynol-10;
c. beeswax in an amount of about 0–30 wt. %;
d. carnauba in an amount of about 0–30 wt. %;
e. PVP in an amount of about 0–20 wt. %;
f. propylene glycol in an amount of about 0–20 wt. %;
g. glyceryl stearate in an amount of about 0–15 wt. %;
h. stearic acid in an amount of about 0–10 wt. %;
i. propylene glycol stearate in an amount of about 0–10 wt. %;
j. oleic acid in an amount of about 0–10 wt. %;
k. polybutene in an amount of about 0–10 wt. %;
l. magnesium aluminum silicate in an amount of about 0–5 wt. %;
m. phenoxyethanol in an amount of about 0–5 wt. %;
n. cellulose gum in an amount of about 0–5 wt. %;
o. methylparaben in an amount of about 0–5 wt. %;
p. propylparaben in an amount of about 0–5 wt. %;
q. tetrasodium EDTA in an amount of about 0–5 wt. % and
r. simethicone in an amount of about 0.01–5 wt. %.

4. A mascara composition as defined in claim 1, wherein the mascara composition is substantially dried in less than about 3 minutes after application of the mascara composition to a person's eyelashes as a result of the drying system.

5. A mascara composition as defined in claim 1, wherein the mascara composition is substantially dried in less than about 2 minutes after application of the mascara composition to a person's eyelashes as a result of the drying system.

6. A mascara composition as defined in claim 1, wherein the mascara composition is substantially dried in less than about 1 minute after application of the mascara composition to a person's eyelashes as a result of the drying system.

7. A mascara composition as defined in claim 1, wherein the mascara composition is at least partially water resistant upon drying.

8. A mascara composition as defined in claim 1, wherein the mascara composition is substantially water soluble after drying.

9. A mascara composition as defined in claim 1, wherein the drying system is included in an amount in a range from about 5% to about 30% by weight of the mascara composition.

10. A mascara composition as defined in claim 1, wherein the drying system is included in an amount in a range from about 8% to about 20% by weight of the mascara composition.

11. A mascara composition as defined in claim 1, wherein the diluent comprises water.

12. A mascara composition as defined in claim 1, wherein the diluent includes a volatile solvent.

13. A mascara composition as defined in claim 12, wherein the volatile solvent is selected from the group consisting of alcohols, aldehydes, ketones, esters, and mixtures of the foregoing.

14. A mascara composition as defined in claim 1, wherein the antifoaming agent comprises simethicone.

15. A mascara composition as defined in claim 12, wherein the simethicone is included in an amount in a range from about 0.01% to about 5% by weight of the mascara composition.

16. A mascara composition as defined in claim 1, further comprising:

a. beeswax in an amount up to about 30% by weight of the composition;
b. carnauba in an amount up to about 30% by weight of the composition;
c. PVP in an amount up to about 20% by weight of the composition;
d. propylene glycol in an amount up to about 20% by weight of the composition;
e. glyceryl stearate in an amount up to about 50% by weight of the composition;
f. stearic acid in an amount up to about 10% by weight of the composition;
g. propylene glycol stearate in an amount up to about 10% by weight of the composition;
h. oleic acid in an amount up to about 10% of the composition;
i. polybutene in an amount up to about 10% by weight of the composition;
j. magnesium aluminum silicate in an amount up to about 5% by weight of the composition;
k. phenoxyethanol in an amount up to about 5% by weight of the composition;
l. cellulose gum in an amount up to about 5% by weight of the composition;
m. methylparaben in an amount up to about 5% by weight of the composition;
n. propylparaben in an amount up to about 5% by weight of the composition;
o. tetrasodium EDTA in an amount up to about 5% by weight of the composition; and
p. the antifoaming agent including simethicone in an amount up to about 5% by weight of the composition.

* * * * *

UNITED STATES PATENT AND TRADEMARK OFFICE
CERTIFICATE OF CORRECTION

PATENT NO. : 5,800,825
DATED : Sep. 1, 1998
INVENTOR(S) : Alexandra McMullen

It is certified that error appears in the above-identified patent and that said Letters Patent is hereby corrected as shown below:

Col. 1, line 10, after "which" change "arc" to --are--

Col. 7, line 37, after "Beeswax" insert --8%--

Col. 9, line 64, before "said" change "nonoxynol- 10" to --nonoxynol-10--

Col. 10, line 24, after "0-5 wt. %" insert a semicolon

Signed and Sealed this

Fifth Day of October, 1999

Attest:

Q. TODD DICKINSON

*Attesting Officer*  *Acting Commissioner of Patents and Trademarks*